US00PP25979P3

(12) United States Plant Patent
Zary

(10) Patent No.: US PP25,979 P3
(45) Date of Patent: Oct. 13, 2015

(54) HYBRID TEA ROSE PLANT NAMES 'JACNIZEA'

(50) Latin Name: *Rosa hybrida*
Varietal Denomination: JACnizea

(71) Applicant: J & P PARK ACQUISITIONS, INC., Columbia, SC (US)

(72) Inventor: Keith Zary, Troy, OH (US)

(73) Assignee: J & P Park Acquisitions, Inc., Columbia, SC (US)

( * ) Notice: Subject to any disclaimer, the term of this patent is extended or adjusted under 35 U.S.C. 154(b) by 0 days.

(21) Appl. No.: 13/998,639

(22) Filed: Nov. 19, 2013

(65) Prior Publication Data

US 2015/0143593 P1 May 21, 2015

(51) Int. Cl.
*A01H 5/02* (2006.01)

(52) U.S. Cl.
USPC ..... Plt./132

(58) Field of Classification Search
USPC ..... Plt./101, 130, 132
See application file for complete search history.

(56) References Cited

U.S. PATENT DOCUMENTS

| | | | |
|---|---|---|---|
| PP8,279 | P | 6/1993 | McGredy, IV |
| PP8,494 | P | 12/1993 | Tracy |
| PP11,691 | P | 12/2000 | Zary |

*Primary Examiner* — Susan McCormick Ewoldt
(74) *Attorney, Agent, or Firm* — McKee, Voorhees & Sease, PLC

(57) ABSTRACT

A new variety of Hybrid Tea rose suitable for garden decoration, having flowers of cream in the center of the bloom and coral on the edges.

1 Drawing Sheet

Classification: The present invention relates to a new *Rosa hybrida* plant.

Variety denomination: The new plant has the varietal denomination 'JACnizea'.

BACKGROUND OF THE INVENTION

This invention relates to a new and distinct variety of Hybrid Tea Rose. It has as its seed parent the variety known as 'JACnepal' (U.S. Plant Pat. No. 11,691) and as the pollen parent MACgenev (U.S. Plant Pat. No. 8,279).

SUMMARY OF THE INVENTION

Among the features which distinguish the new variety from other presently available and commercial rose cultivars known to the inventor are the following combinations of characteristics: an elegant high-centered bud opening to an large attractive fully open flower of soft cream and coral pink, a strong sweet hyacinth fragrance, strong upright growth, medium length cutting stems and long vase life. The plant has a bushy upright growing habit, suitable for outdoor garden decoration.

Asexual reproduction of the new variety by budding as performed in Kern County, Calif., shows that the foregoing and other distinguishing characteristics come true to form and are established and transmitted through succeeding asexual propagations. 'JACnizea' may be asexually propagated by cuttings, budding and grafting. The budding and grafting successfully occurred on the plant/rootstock *Rosa hybrida* cv. Dr. Huey (not patented).

COMPARISON WITH PARENTS

The new rose may be distinguished from its seed parent, 'JACnepal' by the following combination of characteristics:

whereas 'JACnepal' bears large flowers (about 11 to 13 cm in diameter) of coral coloration , 'JACnizea' bears slightly smaller flowers (about 9.0 to about 11.0 cm in diameter) of cream edged in coral. 'JACnepal' also has a very light fragrance while 'JACnizea' is intensely fragrant.

The new variety may be distinguished from its pollen parent 'MACgenev' by the following combination of characteristics: whereas 'MACgenev' bears large flowers (11 to 13 cm) of soft cream pink coloration, the new variety 'JACnizea' bears significantly smaller flowers (9.0 to 11.0 cm in diameter) of cream edged in coral coloration. 'MACgenev' is also taller by an average of 20 cm than 'JACnizea' (160 to 180 cm versus 140 to 160 cm).

COMPARISON WITH THE CLOSEST COMMERCIALLY AVAILABLE CULTIVAR

The new variety may be distinguished from its closest commercially available cultivar, 'HILaroma' (U.S. Plant Pat. No. 8,494) by the following combination of characteristics: whereas 'HILaroma' bears flowers of cream brushed with rich pink coloration, 'JACnizea' bears flowers of cream edged in coral coloration. 'HILaroma' also has a strong sweet and spicy fragrance, while 'JACnizea' has a very distinctive and intense hyacinth fragrance.

BRIEF DESCRIPTION OF ILLUSTRATION

The accompanying photograph illustrates the new variety and shows the flowering thereof from bud to full bloom depicted in color as nearly correct as it is possible to make in a color illustration of the character. The plant parts used for the photograph came from 3 to 4 year-old rose plants of the new variety grown outdoors in Tipp City, Ohio in the month July. Throughout this specification, color references and/or values are based upon The Colour Chart of The Royal Horticultural Society (2001) except where common terms of color definition are employed.

DESCRIPTION OF THE NEW VARIETY

The following description is of 3 to 4 year-old rose plants of the new variety grown outdoors in Tipp City, Ohio in the month of July. Phenotypic expression may vary with environmental, cultural and climatic conditions, as well as differences in conditions of light and soil.

FLOWER

The new variety bears medium sized flowers borne one per stem or occasionally in small clusters of three. Flowers are borne on strong, medium length stems (about 40 to about 60 cm with a diameter of 8 to 10 mm). Outdoors, the plant blooms abundantly and nearly continuously during the growing season. The flowers have a very strong hyacinth-like fragrance.

BUD

The bud is about 3.0 to 3.5 cm long and about 2.0 to 2.5 cm in diameter when the petals start to unfurl. The bud is long and pointed ovoid in shape. As the petals open (after the calyx breaks), the bud is about 3.0 to 3.5 cm in diameter at the widest point, about 3.5 to 4.0 cm in length, and moderately ovoid in form. When the sepals first divide, the bud color is 158D. When half blown, the upper sides of the petals are 158D in color on the majority of petals except on the outside of the bloom where the petals are 50 C and the lower sides of the petals are 158D.

The sepals are about 3.0 cm in length and about 0.9 cm in width at the widest point. The color of the sepal is 138B on the upper surface and 146A on the lower surface. The outer surface of the sepal is smooth and bears 1 or 2 foliaceous appendages. The inner surface of the sepal is covered with fine wooly tomentum; sepal margins are lined with very few stipitate glands and hairs.

The peduncle is stiff and erect, and quite short in length for hybrid teas (about 4.0 cm), and of average caliper (about 0.4 cm in diameter). It is quite smooth with many very small glands. Peduncle color is 146C, often with an overlay of 183D.

The receptacle of the flower is funnel shaped and medium in size (about 1.0 cm in length and about 0.8 cm in diameter). Its surface is smooth. The receptacle color is 146B.

BLOOM

When fully open, the bloom ranges from about 9.0 to 11.0 cm in diameter. Petalage is double with about 35-40 petals under normal conditions. When first open, the bloom form is high-centered and the petals are imbricated with petal edges somewhat reflexed downward. The bloom flattens over time exposing the anthers and pistils.

PETALS

The substance of the petals is thick and leathery with a smooth surface. The petals are about 5.0 to 5.5 cm in length and about 4.5 to 4.8 cm in width at the widest point. The shape of the petals is orbicular to obcordate and flat with obtuse to obcordate apices. Petal margins are entire. Petals are arranged in an imbricated fashion and drop off of the plant cleanly before dying. Petals last on the plant for about 7 days. As a cut flower the petals last about 9 days.

Petaloids number from 1 to 5 and are 158D in color. Petaloids are about 1.9 to about 2.5 cm in length and about 1.0 to about 2.5 cm in width at the widest point. Petaloids are irregularly-shaped, somewhat oblong to spatulate with rounded apices.

NEWLY OPENED FLOWER

The upper side of the petals are 158D in color on the newly opened flower. The reverse side of the petals are 158D in color. The base of the petals has a large color spot of about 8-12 mm in length and 7 to 10 mm in width with a color of 3C. The under and upper surface colors of the petaloids are similar in coloration to the upper and under surfaces of the petals.

The general tonality at the end of the first day is no change.

THREE-DAY-OLD FLOWER

At the end of the third day the tonality is unchanged in the center of the flower but the petals on the outside of the flower intensify in color to 50C. The base color spot changes from 3C in color to 2C in color. The under and upper surface colors of the petaloids are similar in coloration to the upper and under surfaces of the petals in the center of the flower.

The flower finishes by the 50C color slowly spreading across the flower as the flower ages. By day 7 outside the 50C color is dominate. As a cut flower inside, this color change does not occur and the flower essentially stays the color of the stage in which it was cut.

MALE REPRODUCTIVE ORGANS

Stamens average about 60 to 70 in number and are about 1.0 to 1.2 cm in length. Anthers are 4 mm in length with color of 20C. Anthers are arranged regularly around the styles and mixed with petaloids.

Filaments are of somewhat long length (about 6.0 to 8.0 mm) most with anthers. Filaments are 27D in color. Pollen is scarce and is 164C in color.

FEMALE REPRODUCTIVE ORGANS

Pistils average about 55 per flower. Styles are moderately even and are about 3 to 4 mm in length moderately heavy in caliper, and bunched. Style color is 184C.

Stigmas are 158C in color and 0.1 cm in length. Ovaries are usually all enclosed in the calyx.

Hips have not been observed on this variety when grown Tipp City, Ohio. Artificial pollination has not been attempted in this variety.

FOLIAGE

The compound leaves are usually comprised of three to seven leaflets and are borne abundantly. The five-leaflet leaves are about 11 cm long and 8 cm wide.

The terminal leaflets are pointed oval in shape. The base is rounded oblique in shape and the apex shape is acuminate. The upper side of the leaves is leathery and glossy with a single serrated edge. The terminal leaflets are about 5.0 to 5.5 cm in length and about 3.0 to 3.3 cm in width at the widest point.

New foliage is 178A in color on the upper side and 183A in color on the lower side. Old foliage is 137A on the upper side and 138B on the lower side.

The vein color of the leaves is 146C and the venation pattern is reticulate.

The rachis is average in caliper and rough. The upper side is shallowly grooved with many hairs and few stipitate glands on the edges of the grooves. The underside of the rachis is rough with some hairs and few small prickles. The rachis color is 138B.

The stipules are about 9-10 mm in length, 7-8 mm wide and serrated. The auricle is subulate in shape. The stipule color is 138B.

The petiole is average in caliper and rough. The upper side is shallowly grooved with many hairs and few stipitate glands on the edges of the grooves. The underside of the petiole is rough with some hairs and few small prickles. The petiole is about 1.5 to 2.0 cm in length and about 0.1 to about 0.2 cm in width at the widest point. The petiole color is 138B.

The plant displays an above average degree of resistance to rust and powdery mildew as compared to other commercial varieties grown under comparable condition in Tipp City, Ohio. 'JACnizea' is susceptible to black spot but has not been challenged by downy mildew. The plant's winter hardiness is through zone 6 without protection. North of zone 6 winter protection must be supplied.

GROWTH

The plant has a bushy upright growing habit (about 140 to about 160 cm in height and about 100 to 120 cm spread at the widest point), with full branching. It displays very vigorous growth and the canes are 1.5 up to 2.0 cm in diameter.

Stems of new wood are 146D in color. Stems of old wood are 137B in color. The new wood and the old wood bear some large prickles. The Prickles are moderately hooked downward with a short narrow oval base. Prickles are of 0.7 cm in length. Young prickles are 182D in color. When mature prickles are 200D in color.

There are no small prickles on the main stalk or lateral stalks.

I claim:

1. A new and distinct Hybrid Tea rose plant of the variety substantially as described and illustrated herein.

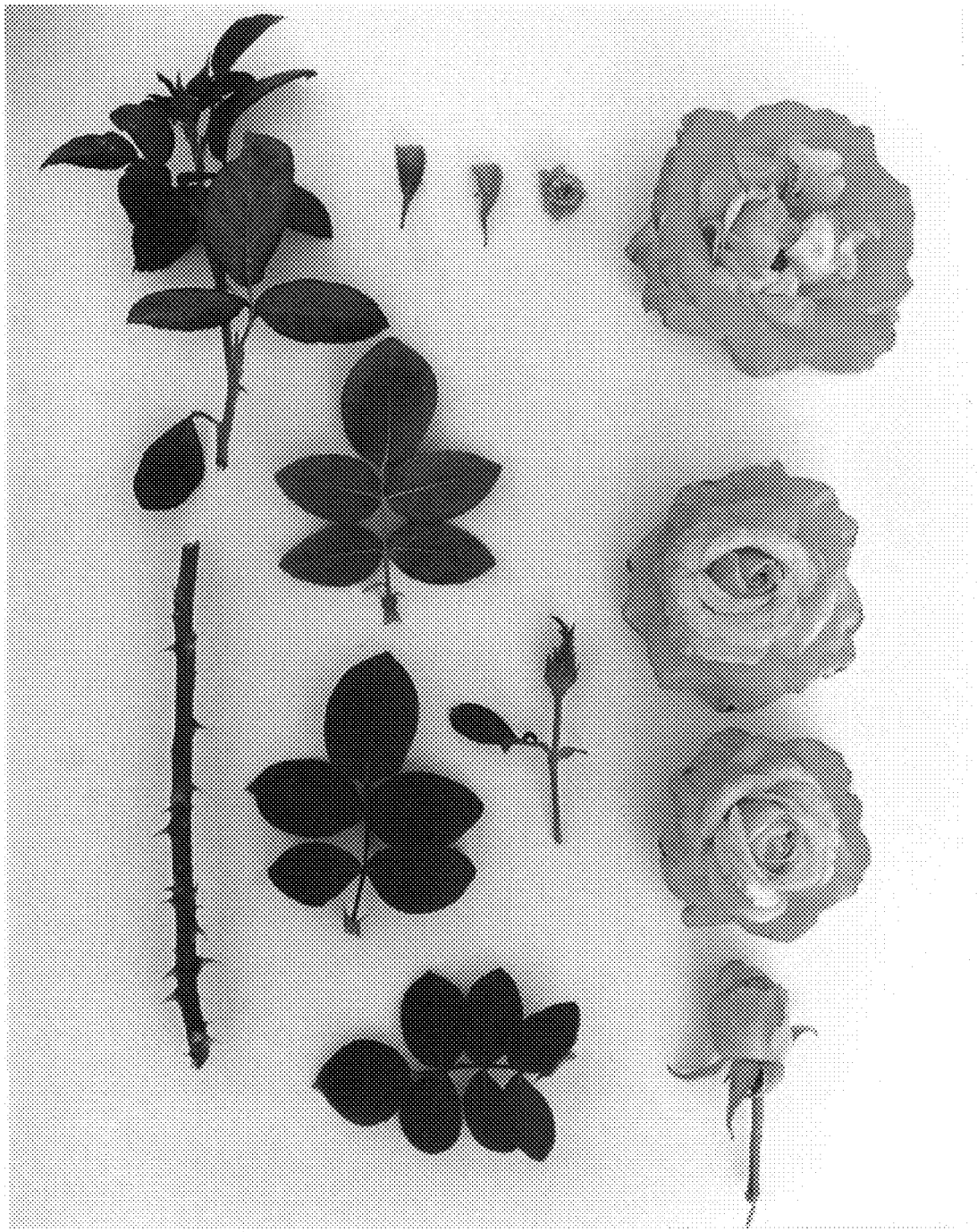

* * * * *